(12) United States Patent
Borysov (10) Patent No.: US 10,919,940 B2
(45) Date of Patent: Feb. 16, 2021

(54) CYCLIC PEPTIDE FOR TREATING CANCER

(71) Applicant: Saint Leo University, Saint Leo, FL (US)

(72) Inventor: Sergiy I. Borysov, Tampa, FL (US)

(73) Assignee: Saint Leo University, Saint Leo, FL (US)

( * ) Notice: Subject to any disclaimer, the term of this patent is extended or adjusted under 35 U.S.C. 154(b) by 22 days.

(21) Appl. No.: 16/388,161

(22) Filed: Apr. 18, 2019

(65) Prior Publication Data

US 2019/0359654 A1 Nov. 28, 2019

Related U.S. Application Data

(60) Provisional application No. 62/660,418, filed on Apr. 20, 2018.

(51) Int. Cl.
*C07K 7/64* (2006.01)
*A61P 35/00* (2006.01)
*A61K 45/06* (2006.01)

(52) U.S. Cl.
CPC ............... *C07K 7/64* (2013.01); *A61P 35/00* (2018.01); *A61K 45/06* (2013.01)

(58) Field of Classification Search
None
See application file for complete search history.

(56) References Cited

U.S. PATENT DOCUMENTS 7,384,735 B1 * 6/2008 Dryja ................. C07K 14/4736
435/320.1
2004/0180058 A1 * 9/2004 Shneider ................. A61P 31/12
424/184.1

* cited by examiner

*Primary Examiner* — Maury A Audet
(74) *Attorney, Agent, or Firm* — Akerman LLP (57) ABSTRACT

The present disclosure generally relates to a circularized peptide for treating cancer. An cyclic peptide is disclosed that has an amino acid sequence selected from Lys-$X_5$-Glu-$X_1$-$X_2$-Gln-Met-Glu-Asp-Asp-$X_3$-$X_4$ (SEQ ID NO: 3), (SEQ ID NO: 4), Lys-Gly-$X_6$-Val-Leu-Gln-Met-$X_7$-$X_8$-$X_9$-Leu-Val (SEQ ID NO: 5), Lys-$X_5$-Glu-$X_1$-$X_2$-Gln-$X_{12}$-Glu-Asp-Asp-$X_3$-$X_4$ (SEQ ID NO: 9), and $X_{10}$-$X_5$-$X_6$-Val-Leu-Gln-Met-Glu-Asp-$X_9$-$X_3$-$X_4$ (SEQ ID NO: 10). The amino acids $X_1$, $X_2$, $X_3$, and $X_4$ can be each independently valine, leucine, isoleucine, or alanine; $X_5$ can be glycine, alanine, leucine, isoleucine, or valine; $X_6$, $X_7$, $X_8$, and $X_9$ can be each independently glutamic acid or asparagine; $X_{10}$ can be lysine or arginine; $X_{11}$ can be methionine or cysteine; and $X_{12}$ can be methionine or norleucine. The cyclic peptide can have the amino acid sequence Lys-Gly-Glu-Val-Leu-Gln-Met-Glu-Asp-Asp-Leu-Val (SEQ ID NO: 1).

21 Claims, 8 Drawing Sheets

Specification includes a Sequence Listing.

SEQUENCE LISTING

```
<160> NUMBER OF SEQ ID NOS: 10

<210> SEQ ID NO 1
<211> LENGTH: 12
<212> TYPE: PRT
<213> ORGANISM: Homo sapiens

<400> SEQUENCE: 1

Lys Gly Glu Val Leu Gln Met Glu Asp Asp Leu Val
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Generic sequence
<220> FEATURE:
<221> NAME/KEY: MISC_FEATURE
<222> LOCATION: (4)..(4)
<223> OTHER INFORMATION: V, L, I, or A
<220> FEATURE:
<221> NAME/KEY: MISC_FEATURE
<222> LOCATION: (5)..(5)
<223> OTHER INFORMATION: V, L, I, or A
<220> FEATURE:
<221> NAME/KEY: MISC_FEATURE
<222> LOCATION: (11)..(11)
<223> OTHER INFORMATION: V, L, I, or A
<220> FEATURE:
<221> NAME/KEY: MISC_FEATURE
<222> LOCATION: (12)..(12)
<223> OTHER INFORMATION: V, L, I, or A

<400> SEQUENCE: 2

Lys Gly Glu Xaa Xaa Gln Met Glu Asp Asp Xaa Xaa
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: G, V, L, I, or A
<220> FEATURE:
<221> NAME/KEY: MISC_FEATURE
<222> LOCATION: (4)..(4)
<223> OTHER INFORMATION: V, L, I, or A
<220> FEATURE:
<221> NAME/KEY: MISC_FEATURE
<222> LOCATION: (5)..(5)
<223> OTHER INFORMATION: V, L, I, or A
<220> FEATURE:
<221> NAME/KEY: MISC_FEATURE
<222> LOCATION: (11)..(11)
<223> OTHER INFORMATION: V, L, I, or A
<220> FEATURE:
<221> NAME/KEY: MISC_FEATURE
<222> LOCATION: (12)..(12)
<223> OTHER INFORMATION: V, L, I, or A

<400> SEQUENCE: 3

Lys Xaa Glu Xaa Xaa Gln Met Glu Asp Asp Xaa Xaa
1               5                   10

<210> SEQ ID NO 4
<211> LENGTH: 12
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: K or R
<220> FEATURE:
<221> NAME/KEY: MISC_FEATURE
<222> LOCATION: (6)..(6)
<223> OTHER INFORMATION: M or C

<400> SEQUENCE: 4

Xaa Gly Glu Val Leu Xaa Met Glu Asp Asp Leu Val
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: E or N
<220> FEATURE:
<221> NAME/KEY: MISC_FEATURE
<222> LOCATION: (8)..(8)
<223> OTHER INFORMATION: E or N
<220> FEATURE:
<221> NAME/KEY: MISC_FEATURE
<222> LOCATION: (9)..(9)
<223> OTHER INFORMATION: E or N
<220> FEATURE:
<221> NAME/KEY: MISC_FEATURE
<222> LOCATION: (10)..(10)
<223> OTHER INFORMATION: E or N

<400> SEQUENCE: 5

Lys Gly Xaa Val Leu Gln Met Xaa Xaa Xaa Leu Val
 1               5                  10

<210> SEQ ID NO 6
<211> LENGTH: 10
<212> TYPE: PRT
<213> ORGANISM: Homo sapiens

<400> SEQUENCE: 6

Gly Glu Val Leu Gln Met Glu Asp Asp Leu
 1               5                  10

<210> SEQ ID NO 7
<211> LENGTH: 8
<212> TYPE: PRT
<213> ORGANISM: Homo sapiens

<400> SEQUENCE: 7

Glu Val Leu Gln Met Glu Asp Asp
 1               5

<210> SEQ ID NO 8
<211> LENGTH: 6
<212> TYPE: PRT
<213> ORGANISM: Homo sapiens

<400> SEQUENCE: 8

Val Leu Gln Met Glu Asp
 1               5
```

```
<210> SEQ ID NO 9
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: G, V, L, I, or A
<220> FEATURE:
<221> NAME/KEY: MISC_FEATURE
<222> LOCATION: (4)..(4)
<223> OTHER INFORMATION: V, L, I, or A
<220> FEATURE:
<221> NAME/KEY: MISC_FEATURE
<222> LOCATION: (5)..(5)
<223> OTHER INFORMATION: V, L, I, or A
<220> FEATURE:
<221> NAME/KEY: MISC_FEATURE
<222> LOCATION: (7)..(7)
<223> OTHER INFORMATION: M or Nle
<220> FEATURE:
<221> NAME/KEY: MISC_FEATURE
<222> LOCATION: (11)..(11)
<223> OTHER INFORMATION: V, L, I, or A
<220> FEATURE:
<221> NAME/KEY: MISC_FEATURE
<222> LOCATION: (12)..(12)
<223> OTHER INFORMATION: V, L, I, or A

<400> SEQUENCE: 9

Lys Xaa Glu Xaa Xaa Gln Xaa Glu Asp Asp Xaa Xaa
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: K or R
<220> FEATURE:
<221> NAME/KEY: MISC_FEATURE
<222> LOCATION: (2)..(2)
<223> OTHER INFORMATION: G, V, L, I, or A
<220> FEATURE:
<221> NAME/KEY: MISC_FEATURE
<222> LOCATION: (3)..(3)
<223> OTHER INFORMATION: E or N
<220> FEATURE:
<221> NAME/KEY: MISC_FEATURE
<222> LOCATION: (10)..(10)
<223> OTHER INFORMATION: E or N
<220> FEATURE:
<221> NAME/KEY: MISC_FEATURE
<222> LOCATION: (11)..(11)
<223> OTHER INFORMATION: V, L, I, or A
<220> FEATURE:
<221> NAME/KEY: MISC_FEATURE
<222> LOCATION: (12)..(12)
<223> OTHER INFORMATION: V, L, I, or A

<400> SEQUENCE: 10

Xaa Xaa Xaa Val Leu Gln Met Glu Asp Xaa Xaa Xaa
1               5                   10
```

CYCLIC PEPTIDE FOR TREATING CANCER

RELATED APPLICATIONS

The present patent document claims the benefit of priority under 35 U.S.C. § 119(e) to U.S. Provisional Patent Application No. 62/660,418, filed on Apr. 20, 2018, which is hereby incorporated by reference in its entirety.

REFERENCE TO SEQUENCE LISTING

A sequence listing entitled "16361-5_Sequence-Listing_190809" is an ASCII text file and is incorporated herein by reference in its entirety. The text file was created on Aug. 9, 2019 and is 3.84 KB in size.

BACKGROUND

1. Field of the Invention

The present disclosure generally relates to a circularized peptide for treating cancer. More particularly, a circularized portion of retinoblastoma (Rb) tumor suppressor protein inhibits helicase activity and can inhibit growth of cancer cells.

2. Description of the Related Art

Cancer involves uninhibited dividing of cells and spreading of those cells throughout the body. Normal cells in the body divide in a process that involves several stages and a host of proteins and signaling molecules. When proteins involved in the cell division process become impaired, cancer can result. For example, cells can express tumor suppressor proteins that prevent uncontrolled DNA replication and cell division.

The retinoblastoma (Rb) tumor suppressor protein inhibits helicase activity, thereby exhibiting a growth repressive function. Helicases are enzymes that separate double-stranded DNA into replicable single strands. RbN with exon deletions in the N-terminal domain can be found in patients with hereditary retinoblastomas. Mutations or deletions in the Rb tumor suppressor gene occurs in other cancer types, such as osteosarcoma, and breast and small cell lung cancers. Also, malfunctioning regulatory components of the Rb pathway is a hallmark of human cancers.

Until recently, the mechanism by which RbN suppresses DNA and helicase activity were unknown. It was discovered that the exon 7 domain of RbN is required to inhibit CMG helicase activity. However, it was unknown whether modified portions of the RbN protein could bind helicase and inhibit the growth of cancer cells. Down-regulation of the CMG helicase's activity specifically kills cancer cultured cells, while sparing normal non-cancerous cells (Bryant V L et al. Mol. Cancer Res. 2015, 13(9), p. 1296-305; Ge X Q et al. Genes Dev. 2007, 21(24), p. 3331-41; Zimmerman K M et al. Mol. Cancer Res. 2013, 11(4), p. 370-80; Ibarra A et al. Proc. Natl. Acad. Sci., 2008, 105(26), p. 8956-61).

BRIEF SUMMARY

In some embodiments, a peptide is disclosed that has an amino acid sequence selected from Lys-$X_5$-Glu-$X_1$-$X_2$-Gln-Met-Glu-Asp-Asp-$X_3$-$X_4$ (SEQ ID NO: 3), $X_{10}$-Gly-Glu-Val-Leu-$X_{11}$-Met-Glu-Asp-Asp-Leu-Val (SEQ ID NO: 4), Lys-Gly-$X_6$-Val-Leu-Gln-Met-$X_7$-$X_8$-$X_9$-Leu-Val (SEQ ID NO: 5), Lys-$X_5$-Glu-$X_1$-$X_2$-Gln-$X_{12}$-Glu-Asp-Asp-$X_3$-$X_4$ (SEQ ID NO: 9), and $X_{10}$-$X_5$-$X_6$-Val-Leu-Gln-Met-Glu-Asp-$X_9$-$X_3$-$X_4$ (SEQ ID NO: 10). The amino acids $X_1$, $X_2$, $X_3$, and $X_4$ can be each independently valine, leucine, isoleucine, or alanine; $X_5$ can be glycine, alanine, leucine, isoleucine, or valine; $X_6$, $X_7$, $X_8$, and $X_9$ can be each independently glutamic acid or asparagine; $X_{10}$ can be lysine or arginine; $X_{11}$ can be methionine or cysteine; and $X_{12}$ can be methionine or norleucine. For SEQ ID NO: 10 $X_3$, $X_4$, $X_5$, $X_6$, $X_9$, and $X_{10}$ are each independently optional. The peptide can be circularized.

In some embodiments, the amino acid sequence can be the sequence shown in SEQ ID NO: 3.

In some embodiments, the peptide consists of the amino acid sequence Lys-Gly-Glu-Val-Leu-Gln-Met-Glu-Asp-Asp-Leu-Val (SEQ ID NO: 1).

In some embodiments, the peptide consists of the amino acid sequence Lys-Gly-Glu-$X_1$-$X_2$-Gln-Met-Glu-Asp-Asp-$X_3$-$X_4$ (SEQ ID NO: 2).

In some embodiments, the amino acid sequence can be the sequence shown in SEQ ID NO: 4.

In some embodiments, the amino acid sequence can be the sequence shown in SEQ ID NO: 5.

In some embodiments, the peptide can be labeled with a detectable label.

In some embodiments, the peptide can be conjugated to a cytotoxic molecule, a radioactive molecule, or a hydrophobic group.

In other embodiments, the peptide further comprises a first cysteine conjugated to an amino acid at an N-terminus and a second cysteine conjugated to an amino acid at the C-terminus to circularize the peptide by forming a disulfide bond between the first cysteine at the N-terminus and the second cysteine at the C-terminus.

In some embodiments, the peptide can be circularized by forming an amide bond between an N-terminal amino acid and a C-terminal amino acid.

In certain embodiments, a composition is disclosed that comprises a pharmaceutically acceptable carrier and any peptide described herein.

In other embodiments, a method of inhibiting helicase function is disclosed. The method can include contacting a cell with a helicase-inhibiting amount of any of the peptides described herein.

In some embodiments, a method of treating cancer is disclosed. The method can include administering to a subject having the cancer with a therapeutically effective amount of a peptide comprising an amino acid sequence selected from Lys-$X_5$-Glu-$X_1$-$X_2$-Gln-Met-Glu-Asp-Asp-$X_3$-$X_4$ (SEQ ID NO: 3), $X_{10}$-Gly-Glu-Val-Leu-$X_{11}$-Met-Glu-Asp-Asp-Leu-Val (SEQ ID NO: 4), Lys-Gly-$X_6$-Val-Leu-Gln-Met-$X_7$-$X_8$-$X_9$-Leu-Val (SEQ ID NO: 5), Lys-$X_5$-Glu-$X_1$-$X_2$-Gln-$X_{12}$-Glu-Asp-Asp-$X_3$-$X_4$ (SEQ ID NO: 9), and $X_{10}$-$X_5$-$X_6$-Val-Leu-Gln-Met-Glu-Asp-$X_9$-$X_3$-$X_4$ (SEQ ID NO: 10) wherein $X_1$, $X_2$, $X_3$, and $X_4$ are each independently valine, leucine, isoleucine, or alanine; $X_5$ is glycine, alanine, leucine, isoleucine, or valine; $X_6$, $X_7$, $X_8$, and $X_9$ are each independently glutamic acid or asparagine; $X_{10}$ is lysine or arginine; $X_{11}$ is methionine or cysteine; and $X_{12}$ can be methionine or norleucine. For SEQ ID NO: 10 $X_3$, $X_4$, $X_5$, $X_6$, $X_9$, and $X_{10}$ are each independently optional. The peptide may be circularized, and the cancer may be selected from lung cancer, liver cancer, pancreatic cancer, testicular cancer, pancreatic ductal adenocarcinoma, colorectal carcinoma, osteosarcoma, cervical cancer, and breast cancer.

In some embodiments, the amino acid sequence as shown in SEQ ID NO: 3 can be administered to the subject having cancer.

In some embodiments, the peptide administered to the subject having cancer comprises the amino acid sequence Lys-Gly-Glu-Val-Leu-Gln-Met-Glu-Asp-Asp-Leu-Val (SEQ ID NO: 1).

In some embodiments, the cancer is testicular cancer.

In some embodiments, the peptide can be administered via a route selected from the group consisting of oral administration, nasal administration, administration by inhalation, rectal administration, intraperitoneal injection, intravascular injection, subcutaneous injection, transcutaneous administration, and intramuscular injection.

In some embodiments, the method of treating cancer can include administering a chemotherapeutic agent.

In other embodiments, a kit is disclosed. The kit can include a container containing, a peptide comprising an amino acid sequence selected from Lys-$X_5$-Glu-$X_1$-$X_2$-Gln-Met-Glu-Asp-Asp-$X_3$-$X_4$ (SEQ ID NO: 3), $X_{10}$-Gly-Glu-Val-Leu-$X_{11}$-Met-Glu-Asp-Asp-Leu-Val (SEQ ID NO: 4), and Lys-Gly-$X_6$-Val-Leu-Gln-Met-$X_7$-$X_8$-$X_9$-Leu-Val (SEQ ID NO: 5), wherein $X_1$, $X_2$, $X_3$, and $X_4$ are each independently valine, leucine, isoleucine, or alanine; $X_5$ is glycine, alanine, leucine, isoleucine, or valine; $X_6$, $X_7$, $X_8$, and $X_9$ are each independently glutamic acid or asparagine; $X_{10}$ is lysine or arginine; $X_{11}$ is methionine or cysteine; wherein the peptide is circularized; and instructional materials teaching the use of the peptide in inhibiting helicase function and/or treatment of cancer.

In some embodiments, the kit contains a peptide comprising the amino acid sequence Lys-Gly-Glu-Val-Leu-Gln-Met-Glu-Asp-Asp-Leu-Val (SEQ ID NO: 1).

In some embodiments, a peptide is disclosed that comprises an amino acid sequence of SEQ ID NO: 1 or a functional homologue thereof having at least 90% identity with SEQ ID NO: 1.

The foregoing outlines the features and technical advantages of the present disclosure in order that the detailed description that follows may be better understood. Additional features and advantages of the disclosure will be described hereafter that form the subject of the claims of this application. Those skilled in the art should appreciate that the conception and the specific embodiments disclosed may be readily used as a basis for modifying or designing other embodiments for carrying out the same purposes of the present disclosure. Those skilled in the art that should appreciate such equivalent embodiments do not depart from the spirit and scope of the disclosure as set forth in the appended claims.

BRIEF DESCRIPTION OF THE DRAWINGS

A detailed description of the invention is hereafter described with specific reference being made to the drawings in which.

DETAILED DESCRIPTION

Various embodiments are described below. The relationship and functioning of the various elements of the embodiments may better be understood by reference to the following detailed description. The embodiments, however, are not limited to those illustrated in the drawings and described herein. It should be understood that in certain instances details may have been omitted that are not necessary for an understanding of embodiments disclosed herein, such as—for example—conventional peptide synthesis and purification.

In some embodiments, a peptide is disclosed that has an amino acid sequence selected from SEQ ID NO: 3, SEQ ID NO: 4, SEQ ID NO: 5, SEQ ID NO: 9, and SEQ ID NO: 10. The amino acids $X_1$, $X_2$, $X_3$, and $X_4$ can be each independently valine, leucine, isoleucine, or alanine; $X_5$ can be glycine, alanine, leucine, isoleucine, or valine; $X_6$, $X_7$, $X_8$, and $X_9$ can be each independently glutamic acid or asparagine; $X_{10}$ can be lysine or arginine; and can be methionine or cysteine. $X_{12}$ can be methionine or norleucine. For SEQ ID NO: 10 $X_3$, $X_4$, $X_5$, $X_6$, $X_9$, and $X_{10}$ are each independently optional. The peptide can be circularized.

The term "peptide" as used herein, refers to a compound made up of a single chain of D- or L-amino acids or a mixture of D- and L-amino acids joined by peptide bonds.

In some embodiments, the peptide comprises the amino acid sequence Lys-$X_5$-Glu-$X_1$-$X_2$-Gln-$X_{12}$-Glu-Asp-Asp-$X_3$-$X_4$ (SEQ ID NO: 9). In some embodiments, $X_{12}$ can be methionine.

The term "peptide" as used herein is defined as a chain of amino acid residues, usually having a defined sequence.

The variables $X_1$-$X_{12}$ represent conservative substitutions that are believed to not substantially alter the activity of the peptide. The term "conservative substitution" is used in reference to peptides to reflect amino acid substitutions that do not substantially alter the activity or binding affinity of the molecule. Typically, conservative amino acid substitutions involve substitution one amino acid for another amino acid with similar chemical properties, such as charge or hydrophobicity.

For SEQ ID NO: 3, $X_1$, $X_2$, $X_3$, and $X_4$ can be each independently valine, leucine, or isoleucine. In some embodiments, $X_1$ and $X_4$ are valine. In some embodiments, $X_2$ and $X_3$ can be leucine.

For SEQ ID NO: 4, $X_{10}$ can be lysine. In some embodiments, can be methionine.

For SEQ ID NO: 5, $X_6$ can be glutamic acid. In some embodiments, $X_7$ can be glutamic acid. In some embodiments, $X_8$ can be aspartic acid. In some embodiments, $X_9$ can be aspartic acid.

For SEQ ID NO: 9, $X_{12}$ can be methionine or norleucine. In some embodiments, $X_{12}$ is methionine. In some embodiments, $X_{12}$ is norleucine.

For SEQ ID NO: 10, $X_3$, $X_4$, $X_5$, $X_6$, $X_9$, and $X_{10}$ can each be independently optional. For example, $X_{10}$ may be absent and $X_3$, $X_4$, $X_5$, $X_6$, and $X_9$ may be present resulting in an amino acid comprising 11 amino acid residues.

In some embodiments, the amino acid sequence can be the sequence shown in SEQ ID NO: 3. In some embodiments, the peptide consists of the amino acid shown in SEQ ID NO: 3.

In some embodiments, the peptide consists of the amino acid sequence Lys-Gly-Glu-Val-Leu-Gln-Met-Glu-Asp-Asp-Leu-Val (SEQ ID NO: 1).

In some embodiments the peptide consists of the amino acid sequence Gly-Glu-Val-Leu-Gln-Met-Glu-Asp-Asp-Leu (SEQ ID NO: 6), Glu-Val-Leu-Gln-Met-Glu-Asp-Asp (SEQ ID NO: 7), or Val-Leu-Gln-Met-Glu-Asp (SEQ ID NO: 8).

In some embodiments, the peptide consists of the amino acid sequence Lys-Gly-Glu-$X_1$-$X_2$-Gln-Met-Glu-Asp-Asp-$X_3$-$X_4$ (SEQ ID NO: 2).

In some embodiments, the amino acid sequence can be the sequence shown in SEQ ID NO: 4. In some embodiments, the peptide consists of the amino acid shown in SEQ ID NO: 4.

In some embodiments, the amino acid sequence can be the sequence shown in SEQ ID NO: 5. In some embodiments, the peptide consists of the amino acid shown in SEQ ID NO: 5.

In some embodiments, a peptide is disclosed that comprises an amino acid sequence of SEQ ID NO: 1 or a functional homologue thereof having at least 90% identity with SEQ ID NO: 1. In some embodiments, the functional homologue has at least 95% identity with SEQ ID NO: 1.

The sequence similarity between amino acid sequences can be determined using sequence similarity search with the Basic Local Alignment Search Tool (BLAST) program.

Also within the scope of this disclosure are functional analogues or multimers of any of the peptides disclosed herein. The peptides may be a circularized dimer or trimer. The characteristic amino acid sequences of the peptides disclosed herein can be flanked by random amino acid sequences or other amino acid sequences to promote cell internalization or nuclear localization.

The peptides can be branched peptides where the circularized portion is that portion of the amino acid sequence identified in by the sequence identification number, and the branched portion can be a hydrophobic sequence to promote cell internalization. Alternatively, the branched portion could be a nuclear localization sequence to promote accumulation of the peptide in the nucleus of a cell.

In some embodiments, the peptide can be labeled with a detectable label. In some embodiments, the peptide can be conjugated to a cytotoxic molecule, a radioactive molecule, or a hydrophobic group. Such labels may include but are not limited to radioactive label and fluorescent label. Suitable fluorescent labels include, but are not limited to, fluorescein and cyanine dyes.

The peptide can be conjugated to a hydrophobic group. The hydrophobic group can be a sequence of amino acids having hydrophobic side chains or an aliphatic molecule, such as an aliphatic or aromatic compound. For example, the peptide can be modified to include a $C_5$-$C_{18}$ alkyl carbon chain to confer additional hydrophobicity to the peptide. The hydrophobic group can be attached to the side chain of any one of the lysine, aspartic acid, glutamine, methionine, or glutamic acid amino acids.

In other embodiments, the peptide further comprises a first cysteine conjugated to an amino acid at an N-terminus and a second cysteine conjugated to an amino acid at the C-terminus to circularize the peptide by forming a disulfide bond between the first cysteine at the N-terminus and the second cysteine at the C-terminus.

In some embodiments, the peptide can be circularized by forming an amide bond between an N-terminal amino acid and a C-terminal amino acid.

In some embodiments, the peptides are retro-inversion peptides. A "retro-inversion peptide" refers to a peptide with a reversal of the direction of the peptide bond on at least one position, i.e., a reversal of the amino- and carboxy-termini with respect to the side chain of the amino acid. Thus, a retro-inversion analogue has reversed termini and reversed direction of peptide bonds while approximately maintaining the topology of the side chains as in the native peptide sequence. The retro-inversion peptide can contain L-amino acids or D-amino acids, or a mixture of L-amino acids and D-amino acids, up to all of the amino acids being the D-isomer.

The amino acids sequences disclosed herein are not limited to sequences where the amino acids are joined only by amide bonds. In some embodiments, some or all the amide bonds in the peptide can be replaced with isosteric replacements to create a peptide mimetic compound.

The peptides disclosed herein can be synthesized by any known method, such as for example by solid-phase synthesis or by use of recombinant DNA techniques.

Nucleic acid sequences that encode for the selected peptides disclosed herein may be incorporated in a known manner into appropriate expression vectors (i.e. recombinant expression vectors). After the peptides are isolated from the host cell, the peptides can be circularized.

The peptides can be purified by protein purification procedures such as chromatography methods (gel-filtration, ion-exchange and immunoaffinity), by high-performance liquid chromatography (HPLC, RP-HPLC, ion-exchange HPLC, size-exclusion HPLC, high-performance chromatofocusing and hydropho-bic interaction chromatography), or by precipitation (immunoprecipitation).

In certain embodiments, a composition is disclosed that comprises a pharmaceutically acceptable carrier and any peptide described herein.

A pharmaceutically acceptable carrier can include any molecule or particle that facilitates delivery of the peptide to the cells. The peptide can be covalently or non-covalently coupled to the carrier. Examples of suitable carriers include, but are not limited to, lipids, liposomes, microspheres of gold or polystyrene, poly(lactic-co-glycolic acid) (PLGA) particles, or hydrophilic polymers, such as polyethylene glycol. Suitable vehicles are described, for example, in "Handbook of Pharmaceutical Additives" (compiled by Michael and Irene Ash, Gower Publishing Limited, Aldershot, England (1995)).

While not being bound by any particular theory, it is believed that once the peptide enters the cytosol of a cell, the peptide can diffuse into the nucleus. A pharmaceutically acceptable carrier may assist the peptide in penetrating the cellular membrane to access the cytosol of the cell, although a carrier is not necessarily required for the peptide to pass through the cell membrane.

The compositions disclosed herein can also include diluents and may be prepared in buffered solutions with the proper osmotic environment and a suitable pH.

In other embodiments, a method of inhibiting helicase function is disclosed. The method can include contacting a cell with a helicase-inhibiting amount of any of the peptides described herein. The helicase-inhibiting amount can range from about 1.0 nM to about 100 µM. In some embodiments, the helicase-inhibiting amount can range from about 0.5 μM to about 50 μM, about 1 μM to about 20 μM, or about 1 μM to about 10 μM.

The helicase-inhibiting amount may depend upon whether the peptide is concomitantly delivered with a transfection agent or a delivery system, such as a liposome or polymeric particle.

In some embodiments, a method of treating cancer is disclosed. The method can include administering to a subject having the cancer with a therapeutically effective amount of a peptide comprising an amino acid sequence selected from SEQ ID NO: 3, SEQ ID NO: 4, SEQ ID NO: 5, SEQ ID NO: 9, wherein $X_1$, $X_2$, $X_3$, and $X_4$ are each independently valine, leucine, isoleucine, or alanine; $X_5$ is glycine, alanine, leucine, isoleucine, or valine; $X_6$, $X_7$, $X_8$, and $X_9$ are each independently glutamic acid or asparagine; $X_{10}$ is lysine or arginine; $X_{11}$ is methionine or cysteine; and $X_{12}$ is methionine or norleucine, wherein the peptide is circularized. The cancer may be lung carcinoma, liver carcinoma, testicular cancer, pancreatic carcinoma, brain glioma, pancreatic ductal adenocarcinoma, colorectal carcinoma, osteosarcoma, cervical cancer, or breast cancer.

An "effective amount", is defined as an amount effective at dosages and for periods of time necessary to achieve the desired result of inhibiting cancerous cell growth. A therapeutically effective amount of a substance may vary according to factors such as the disease state/health, age, sex, and weight of the recipient. The effective amount will also depend on the chosen route of administering the peptide.

In some embodiments, the peptide can be administered via a route selected from the group consisting of oral administration, nasal administration, administration by inhalation, rectal administration, intraperitoneal injection, intravascular injection, subcutaneous injection, transcutaneous administration, and intramuscular injection.

In some embodiments, the amino acid sequence shown in SEQ ID NO: 3 can be administered to the subject having cancer. In some embodiments, the cancer is testicular cancer. In some embodiments, the cancer is breast cancer. In some embodiments, the cancer is brain glioma or brain cancer. In some embodiments, the cancer is liver cancer. In some embodiments, the cancer is colorectal cancer. In some embodiments, the cancer is pancreatic cancer. In some embodiments, the cancer is lung cancer.

In some embodiments, the method of treating cancer can include administering a chemotherapeutic agent. The chemotherapeutic agent can be administered in combination therapy scenarios.

In other embodiments, a kit is disclosed. The kit can include a container containing, a peptide comprising an amino acid sequence selected from SEQ ID NO: 3, SEQ ID NO: 4, SEQ ID NO: 5, and SEQ ID NO: 9, wherein $X_1$, $X_2$, $X_3$, and $X_4$ are each independently valine, leucine, isoleucine, or alanine; $X_5$ is glycine, alanine, leucine, isoleucine, or valine; $X_6$, $X_7$, $X_8$, and $X_9$ are each independently glutamic acid or asparagine; $X_{10}$ is lysine or arginine; $X_{11}$ is methionine or cysteine; and $X_{12}$ is methionine or norleucine, wherein the peptide is circularized; and instructional materials teaching the use of the peptide in inhibiting helicase function and/or treatment of cancer.

In some embodiments, the kit contains a peptide comprising the amino acid sequence of SEQ ID NO: 1.

EXAMPLES

Example 1

The amide cyclic peptide of SEQ ID NO: 1 was synthesized using solid-phase synthesis. The product was purified using HPLC to a purity of about 99%. The theoretical molecular weight of the peptide was 1357.57 g/mol and was confirmed using mass spectroscopy. The final peptide contained about 42% hydrophobic amino acids, about 33% acidic amino acids, about 8% basic amino acids, and about 17% neutral amino acids.

Example 1

Human recombinant CMG helicase was co-incubated with Peptide 7N (amide cyclic of SEQ ID NO: 1) peptide in the 1-5 nM range and subjected to an in vitro activity assay with Y-shaped oligonucleotides as a substrate.

Figure 1A:
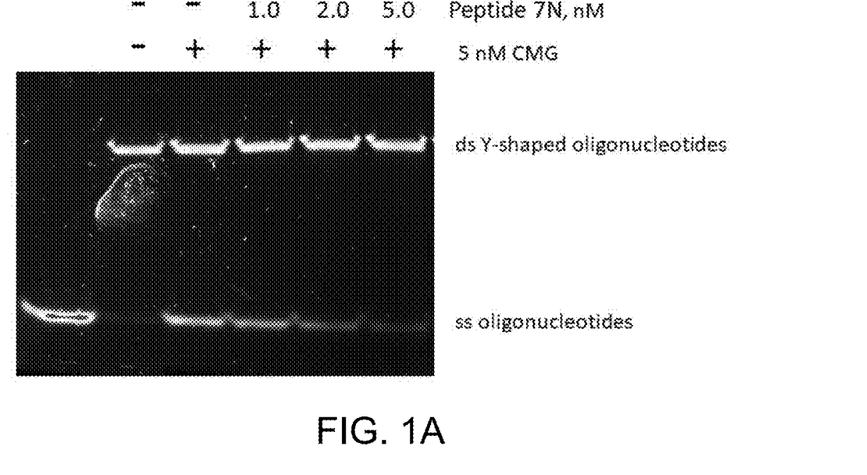
FIG. 1A is an image of an TBE-PAGE gel that shows that the Peptide 7N peptide (amide cyclic of SEQ ID NO: 1) directly inhibits human recombinant CMG helicase in vitro.
Figure 1B:
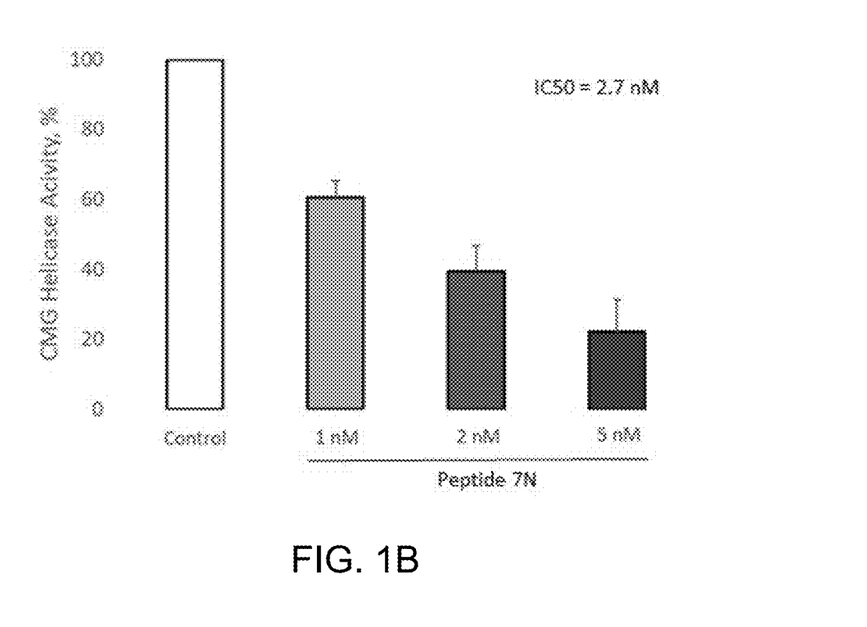
FIG. 1B is a quantitative graphical representation of the DNA bands shown in FIG. 1A.

About 5 nM of CMG helicase was pre-incubated with 1.0, 2.0, or 5.0 nM of Peptide 7N peptide for 20 minutes on ice. In vitro helicase reactions containing partially annealed Y-shaped oligonucleotides as substrate were fired by the addition of 0.5 mM ATP as described previously (Kang Y H et al. PNAS, 2012, 109(16), p. 6042-6047). Reactions were incubated at 37° C. for 45 minutes, stopped with 4 μL of 6× stop solution, and separated by 10% PAGE. To visualize DNA bands, the gel was stained using SYBR Gold nucleic acid stain. Densities of single-stranded DNA bands were quantified by using Image Lab software, and normalized against control. FIG. 1A and FIG. 1B show that the Peptide 7N peptide inhibited CMG helicase in a robust dose-dependent manner.

Example 2

We studied whether the CMG helicase inhibiting Peptide 7N affects viability of human embryonal testicular carcinoma NTERA-2 cells. Pierce Protein Transfection reagent (Thermo Scientific, 89850) was used to deliver peptide to the cultured cells. Transfected cells were allowed to go through two division cycles (48 hours) port-transfection, after which amounts of alive cells were determined by using a colorimetric CCK-8 assay (Dojindo Molecular Technologies, Inc.).

Figure 2:
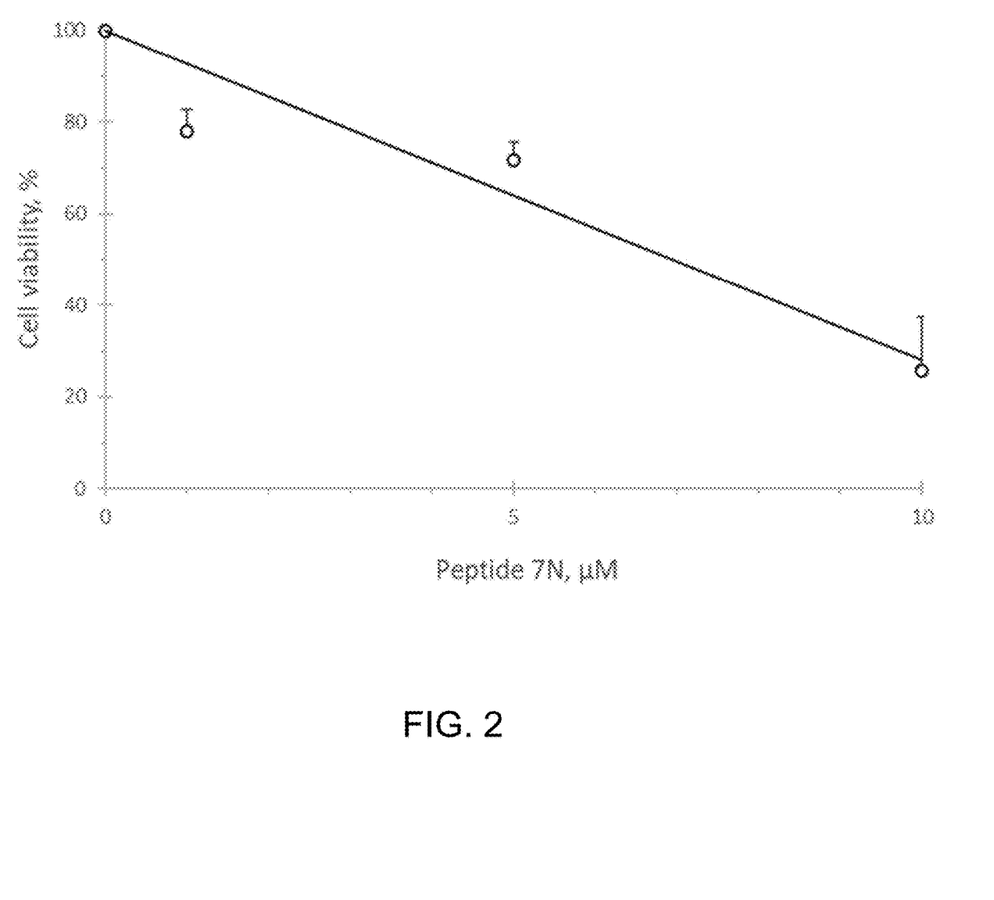
FIG. 2 shows the viability of human embryonal testicular carcinoma cells in the presence of different concentrations of Peptide 7N (amide cyclic of SEQ ID NO: 1)

Human embryonal testicular carcinoma cells (NTERA-2 from ATCC #CRL-1973) were transfected with 1-10 μM Peptide 7N for 4.0 hours, incubated in a complete media for 48 hours, and assessed for viability by using a CCK-8 colorimetric assay. FIG. 2 shows that the peptide effectively inhibited proliferation of NTERA-2 cells in the range of 1-10 μM concentrations.

Example 3

NTERA-2 cells were transfected with 2 μM of FITC-labeled Peptide 7N peptide for 4.0 hours, fixed with 3.6% formaldehyde, and visualized by fluorescence microscopy (images not shown). By using fluorescently-labeled FITC-Peptide 7N, its entry into cells and nuclei was directly confirmed.

Example 4

Non-small cell lung carcinoma (HLF-a and H596) cells and normal embryonic lung fibroblasts (MRC-9) were transfected with 1.25 μM, 2.5 μM, 5.0 μM, or 20.0 μM of peptide 7N (SEQ ID NO: 1) by using Pierce Protein Transfection reagent. Cells were incubated post-transfection for a duration of two doubling periods and assessed for viability by using a cell proliferation CCK-8 assay.

Figure 3:
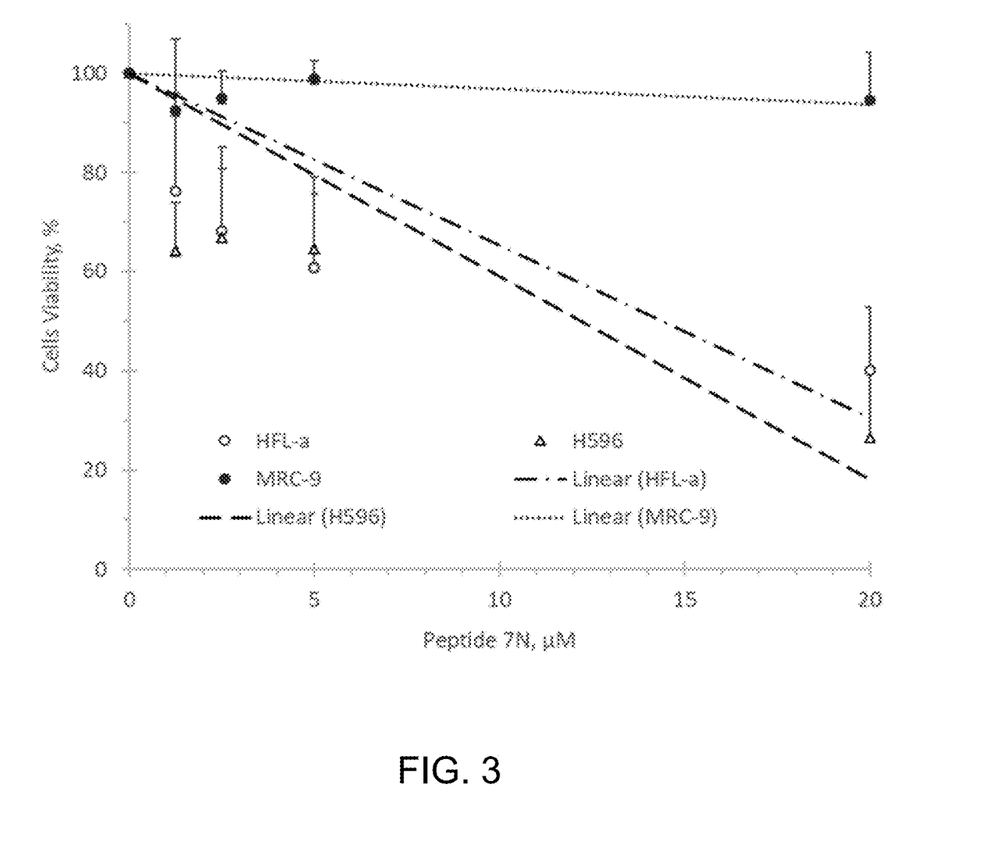
FIG. 3 shows cell viability of lung carcinoma cells treated with Peptide 7N.

FIG. 3 shows that peptide 7N decreased proliferation of lung carcinoma cells, while sparing normal lung fibroblasts.

Example 5

Figure 4:
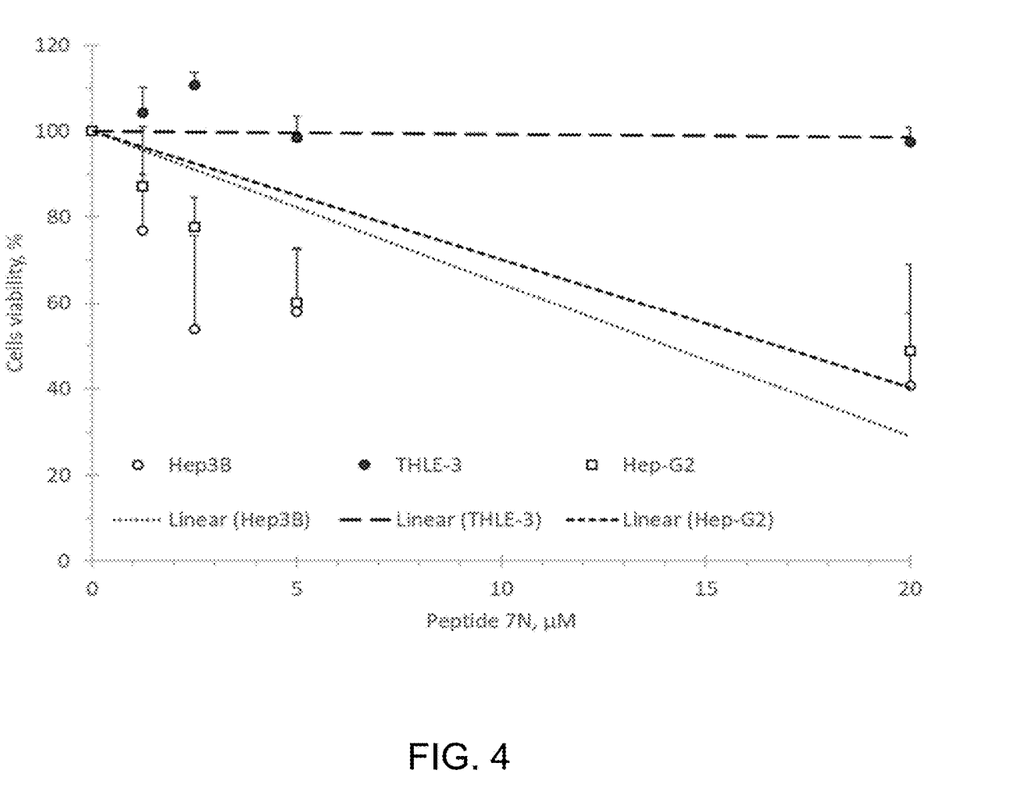
FIG. 4 shows cell viability of liver carcinoma cells treated with Peptide 7N, while sparing immortalized normal liver cells.

Hepatocellular carcinoma (Hep3B and Hep-G2) and immortalized normal liver (THLE-3) cells were transfected with 1.25 µM, 2.5 µM, 5.0 µM, or 20.0 µM of peptide 7N by using Pierce Protein Transfection reagent. Cells were incubated post-transfection for a duration of two doubling periods and assessed for viability by using a cell proliferation CCK-8 assay. FIG. 4 shows that peptide 7N decreased proliferation of liver carcinoma cells, while sparing immortalized normal liver cells.

Example 6

Figure 5:
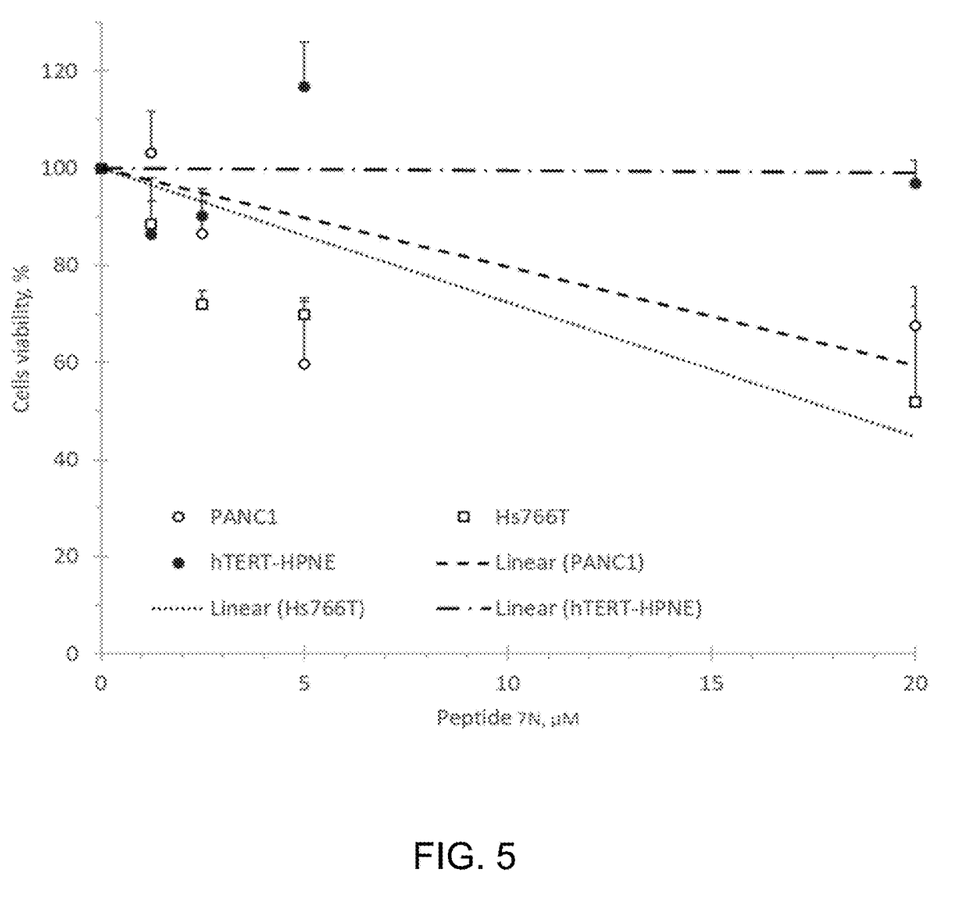
FIG. 5 shows cell viability of pancreatic carcinoma cells treated with Peptide 7N, while sparing immortalized normal pancreatic cells.

Pancreatic carcinoma (PANC-1 and Hs 766T) and immortalized normal pancreatic (hTERT-HPNE) cells were transfected with 1.25 µM, 2.5 µM, 5.0 µM, or 20.0 µM of peptide 7N by using Pierce Protein Transfection reagent. Cells were incubated post-transfection for a duration of two doubling periods and assessed for viability by using a cell proliferation CCK-8 assay. FIG. 5 shows that peptide 7N decreased proliferation of pancreatic carcinoma cells, while sparing immortalized normal pancreatic cells.

Example 7

Figure 6:
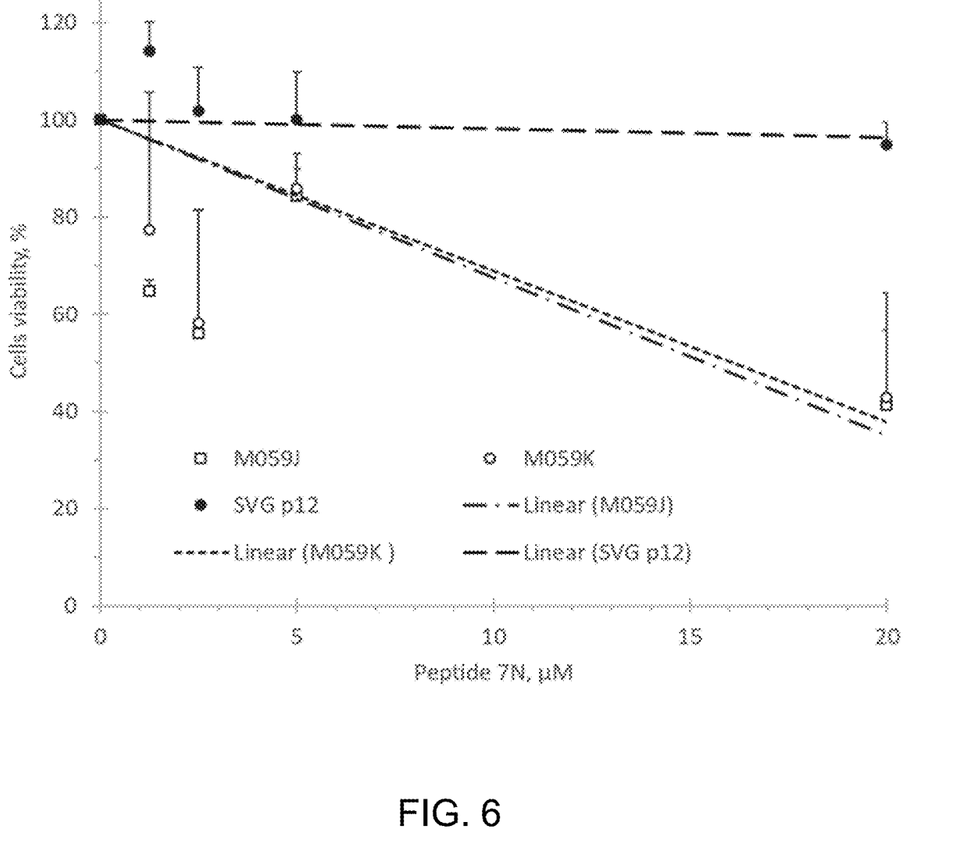
FIG. 6 shows cell viability of brain glioma cells treated with Peptide 7N, while sparing immortalized normal astroglia cells.
Figure 7:
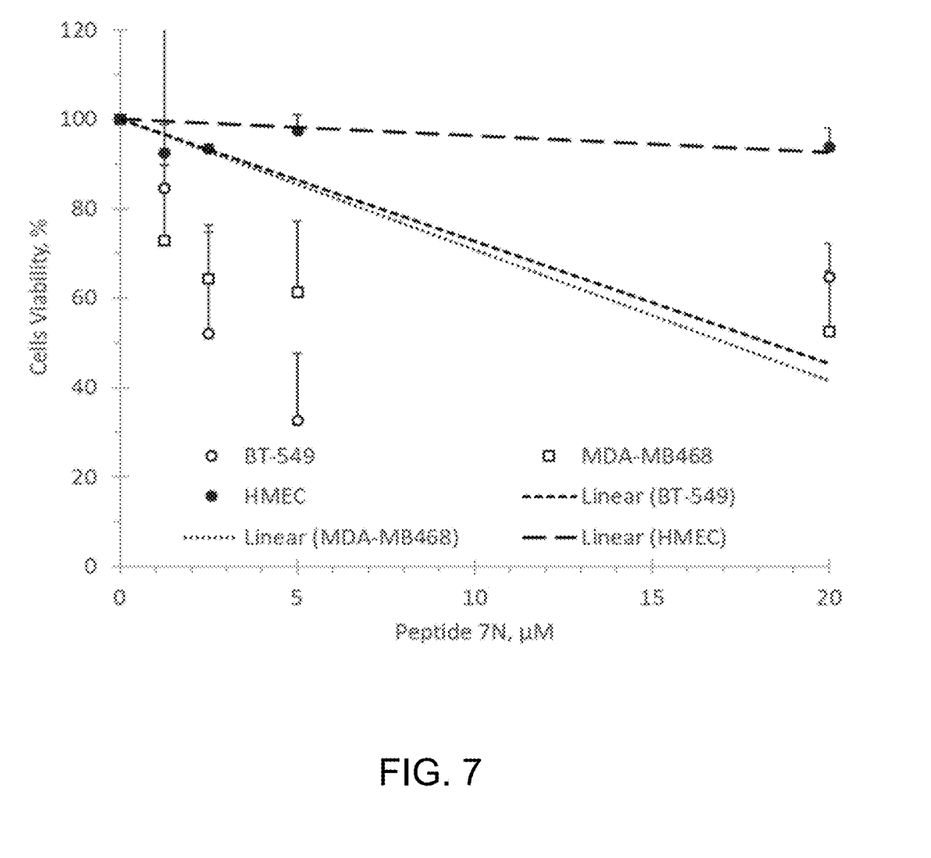
FIG. 7 shows cell viability of breast cancer cells treated with Peptide 7N, while sparing immortalized normal mammary epithelial cells.

Malignant glioblastoma (M059J and M059K) and immortalized normal astroglia (SVG p12) cells were transfected with 1.25 µM, 2.5 µM, 5.0 µM, or 20.0 µM of peptide 7N by using Pierce Protein Transfection reagent. Cells were incubated post-transfection for a duration of two doubling periods and assessed for viability by using a cell proliferation CCK-8 assay. FIG. 6 shows that peptide 7N decreased proliferation of brain glioma cells, while sparing immortalized normal astroglia cells.

Example 8

Peptide 7N decreases proliferation of breast cancer cells, while sparing normal mammary epithelial cells.

Breast adenocarcinoma (MDA-MB468), ductal carcinoma (BT-549), and primary mammary epithelial (HMEC) cells were transfected with 1.25 µM, 2.5 µM, 5.0 µM, or 20.0 µM of peptide 7N by using Pierce Protein Transfection reagent. Cells were incubated post-transfection for a duration of two doubling periods and assessed for viability by using a cell proliferation CCK-8 assay.

Example 9

Figure 8:
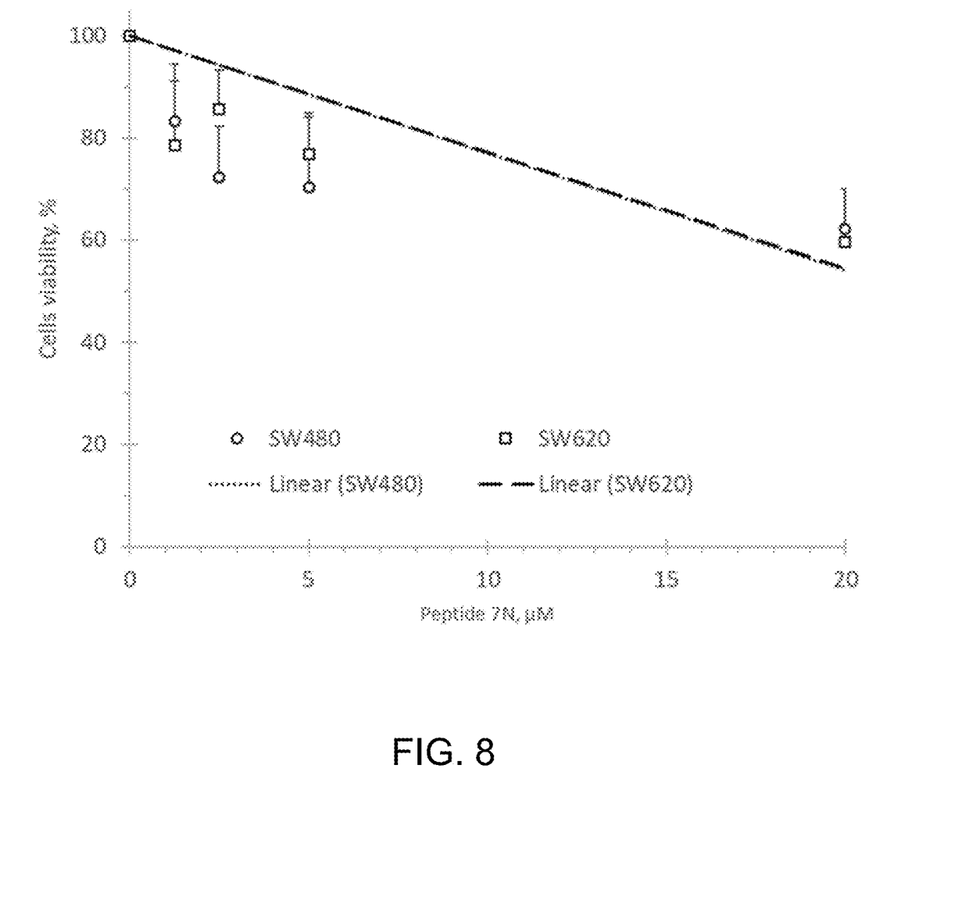
FIG. 8 shows cell viability of colorectal cancer cells treated with Peptide 7N.

Colorectal adenocarcinoma cells (SW480 and SW620) were transfected with 1.25 µM, 2.5 µM, 5.0 µM, or 20.0 µM of peptide 7N by using Pierce Protein Transfection reagent. Cells were incubated post-transfection for a duration of two doubling periods and assessed for viability by using a cell proliferation CCK-8 assay. FIG. 8 shows that peptide 7N decreased proliferation of colorectal cancer cells.

Example 10

Table 1 shows concentrations of peptide 7N at which viabilities of cell lines were reduced to 50%. $IC_{50}$ values were calculated form obtained equations that describe cell viability as a function of peptide concentration.

TABLE 1

| Cell Line | Cancer Type | IC50, µM |
|---|---|---|
| H596 | Adenosquamous lung carcinoma | 12.2 |
| HLF-a | Epidermoid lung carcinoma | 14.4 |
| MRC-9 | Normal embryonic lung fibroblasts | 161.8 |
| Hep3B | Hepatocellular carcinoma | 14.1 |
| Hep-G2 | Hepatocellular carcinoma | 16.7 |
| THLE-3 | Normal immortalized liver cells | 721.5 |
| Hs 766T | Pancreatic carcinoma | 18.1 |
| PANC-1 | Epithelioid pancreatic carcinoma | 24.6 |
| hTERT-HPNE | Normal immortalized pancreatic cells | 1,046.0 |
| M059J | Malignant glioblastoma | 15.4 |
| M059K | Malignant glioblastoma | 16.1 |
| SVG p12 | Normal immortalized astroglia cells | 271.1 |
| MDA-MB468 | Breast adenocarcinoma | 17.1 |
| BT-549 | Breast ductal carcinoma | 18.3 |
| HMEC | Primary mammary epithelial cells | 134.3 |
| SW480 | Colorectal adenocarcinoma | 21.8 |
| SW620 | Colorectal adenocarcinoma | 22.0 |
| NTERA-2 | Testicular cancer | 7.0 |

These results support the idea of targeting CMG helicase for cancer treatment and developing novel anti-cancer therapeutic agents based on peptides disclosed herein.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a peptide" is intended to include "at least one peptide" or "one or more peptides."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is, therefore, intended that such changes and modifications be covered by the appended claims.

What is claimed is:

1. A cyclic peptide selected from the group consisting of:
   (a) the amino acid sequence consisting of the peptide of SEQ ID NO: 1 (Lys-Gly-Glu-Val-Leu-Gln-Met-Glu-Asp-Asp-Leu-Val);
   (b) the amino acid sequence consisting of the peptide of SEQ ID NO: 3 (Lys-$X_5$-Glu-$X_1$-$X_2$-Gln-Met-Glu-Asp-Asp-$X_3$-$X_4$) wherein $X_5$ is glycine and $X_1$, $X_2$, $X_3$, and $X_4$ are each independently valine, leucine, isoleucine, or alanine; and (c) the amino acid sequence consisting of the peptide of SEQ ID NO: 10 ($X_{10}$-$X_5$-$X_6$-Val-Leu-Gln-Met-Glu-Asp-$X_9$-$X_3$-$X_4$) wherein $X_{10}$ is arginine, $X_5$ is glycine, $X_6$ is glutamic acid, $X_9$ is aspartic acid, $X_3$ is leucine, and $X_4$ is valine, wherein the peptide is circularized by forming an amide bond between an N-terminal amino acid and a C-terminal amino acid.

2. The peptide of claim 1, wherein the peptide has the amino acid sequence of SEQ ID NO: 1.

3. The peptide of claim 1, wherein the peptide has the amino acid sequence of SEQ ID NO: 3.

4. The peptide of claim 1, wherein the peptide has the amino acid sequence of SEQ ID NO: 10.

5. The peptide of claim 1, wherein the peptide is labeled with a detectable label.

6. The peptide of claim 1, wherein the peptide is further conjugated to a cytotoxic molecule, a radioactive molecule, or a hydrophobic group.

7. A composition comprising a pharmaceutically acceptable carrier and the peptide of claim 1.

8. A method of inhibiting CMG helicase from separating double stranded DNA into replicable single stranded DNA by administering an effective amount of the peptide of claim 1.

9. The method of claim 8, wherein the peptide has the amino acid sequence of SEQ ID NO:1.

10. The method of claim 8, wherein the peptide has the amino acid sequence of SEQ ID NO: 3.

11. The method of claim 8, wherein the peptide has the amino acid sequence of SEQ ID NO: 10.

12. A method of treating cancer comprising administering a therapeutically effective amount of the peptide of claim 1, wherein the cancer is selected from the group consisting of lung carcinoma, liver carcinoma, testicular cancer, pancreatic carcinoma, brain glioma, pancreatic ductal adenocarcinoma, colorectal carcinoma, osteosarcoma, cervical cancer, and breast cancer.

13. The method of claim 12, wherein the peptide has the amino acid sequence of SEQ ID NO: 1.

14. The method of claim 12, wherein the peptide has the amino acid sequence of SEQ ID NO: 3.

15. The method of claim 12, wherein the peptide has the amino acid sequence of SEQ ID NO: 10.

16. The method of claim 12, wherein the peptide is administered via a route selected from the group consisting of oral administration, nasal administration, administration by inhalation, rectal administration, intraperitoneal injection, intravascular injection, subcutaneous injection, transcutaneous administration, and intramuscular injection.

17. The method of claim 12, further comprising administering a chemotherapeutic agent.

18. A kit comprising: a container containing the peptide of claim 1, and instructional materials teaching the use of the peptide for carrying out a method selected from the group consisting of claim 8 and claim 12.

19. The kit of claim 18, wherein the peptide has the amino acid sequence of SEQ ID NO: 1.

20. The kit of claim 18, wherein the peptide has the amino acid sequence of SEQ ID NO: 3.

21. The kit of claim 18, wherein the peptide has the amino acid sequence of SEQ ID NO: 10.

\* \* \* \* \*